United States Patent [19]

Auth

[11] Patent Number: 4,572,668

[45] Date of Patent: Feb. 25, 1986

[54] APPARATUS AND METHOD FOR PHOTOLUMINESCENT ANALYSIS

[75] Inventor: Gerry L. Auth, Laguna Beach, Calif.

[73] Assignee: MIDAC Corporation, Costa Mesa, Calif.

[21] Appl. No.: 411,603

[22] Filed: Aug. 26, 1982

[51] Int. Cl.$^4$ .................. G01J 3/443; G01N 21/63
[52] U.S. Cl. .................................................. 356/318
[58] Field of Search ..................... 356/301, 317, 318

[56] References Cited

U.S. PATENT DOCUMENTS 4,022,529  5/1977  White ................................. 356/301

OTHER PUBLICATIONS

Barrett et al., *Journal of the Optical Society of America*, vol. 58, No. 3, Mar. 1968, pp. 311-319.
Avanesyan et al., *Sov. J. Quantum Electron*, vol 7, No. 4, Apr. 1977, pp. 403-405.

Primary Examiner—F. L. Evans
Attorney, Agent, or Firm—Thomas J. Plante

[57] ABSTRACT

An optical system is disclosed which significantly enhances the throughput of a grating spectrometer intended to determine impurity concentrations on the surface of semiconductor materials (usually single crystal silicon) used for integrated circuits. The system, which uses a laser beam as the photo-excitation means impinging on a Dewar-contained sample, includes a pre-sample series of lenses which so shapes the laser beam that its shape at the point of impingement on the sample is proportionally similar to the shape of the monochromator slit in the spectrometer. The same lens which provides final focusing of the laser beam on the sample also collects the sample-emitted radiation, which is thereafter focused by suitable optics on the monochromator slit, where it preferably substantially matches the shape of the slit, but slightly overfills the slit.

4 Claims, 12 Drawing Figures

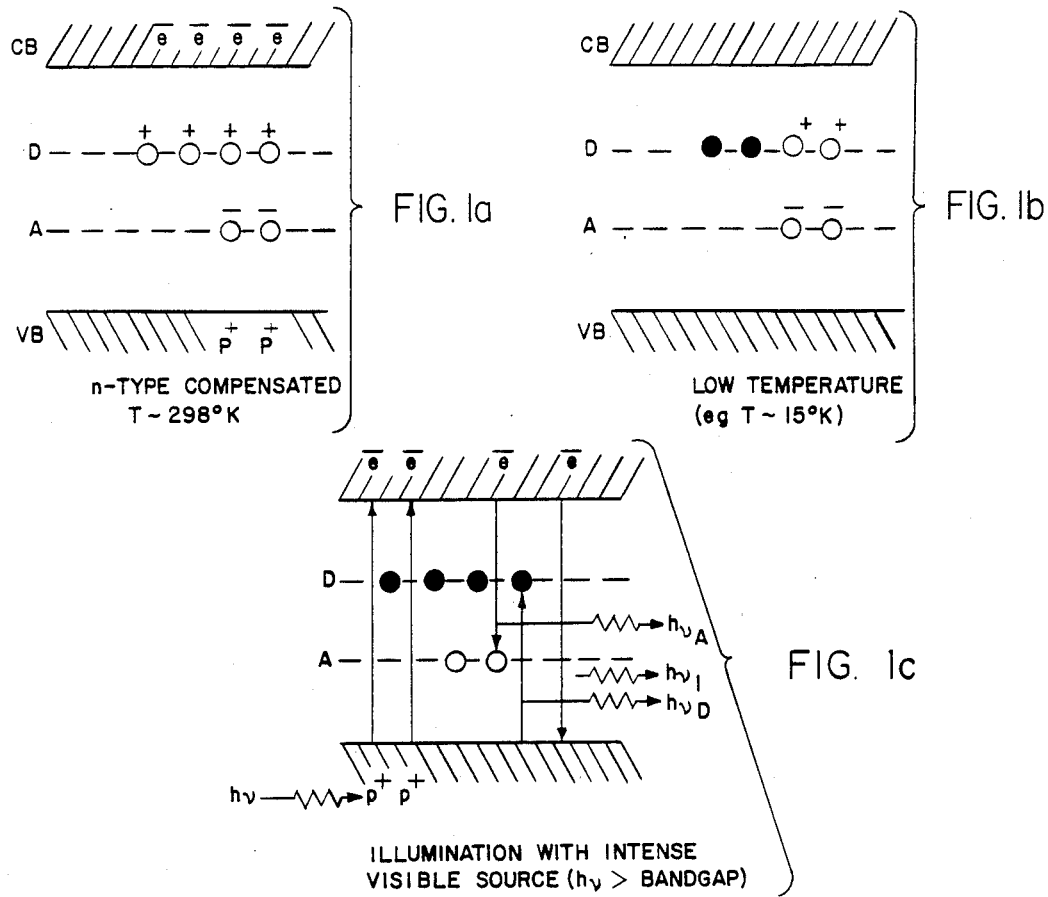
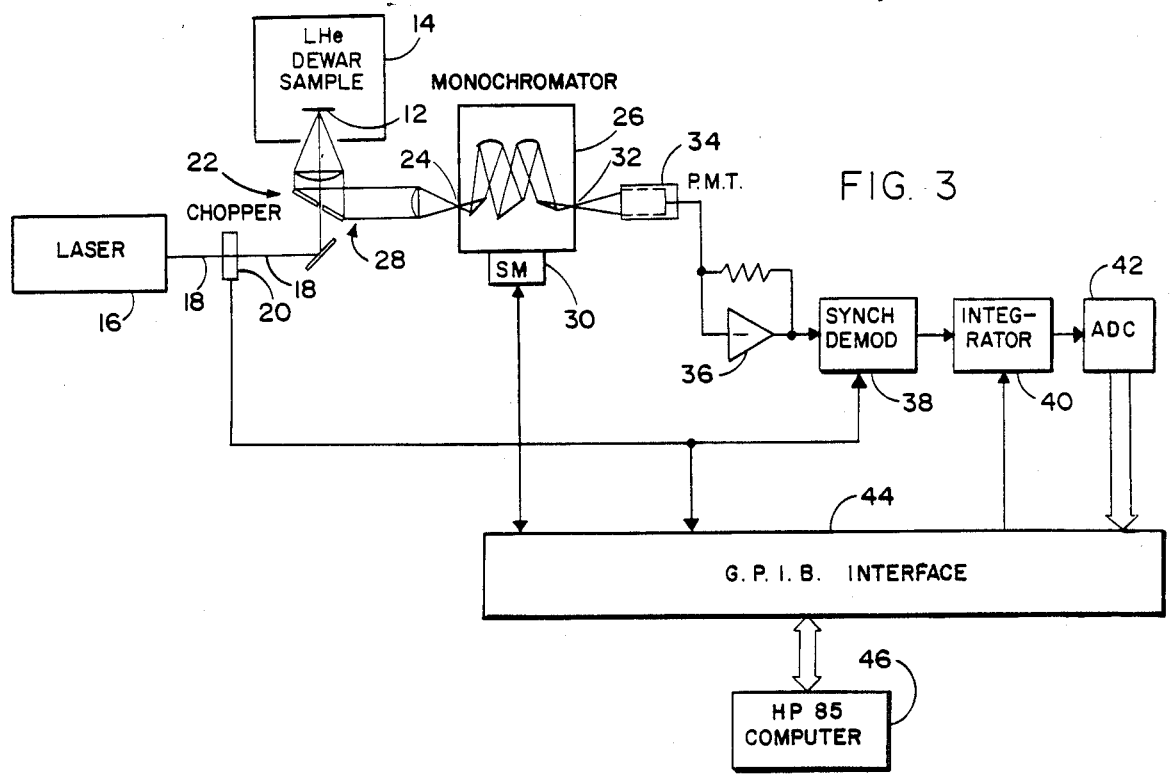

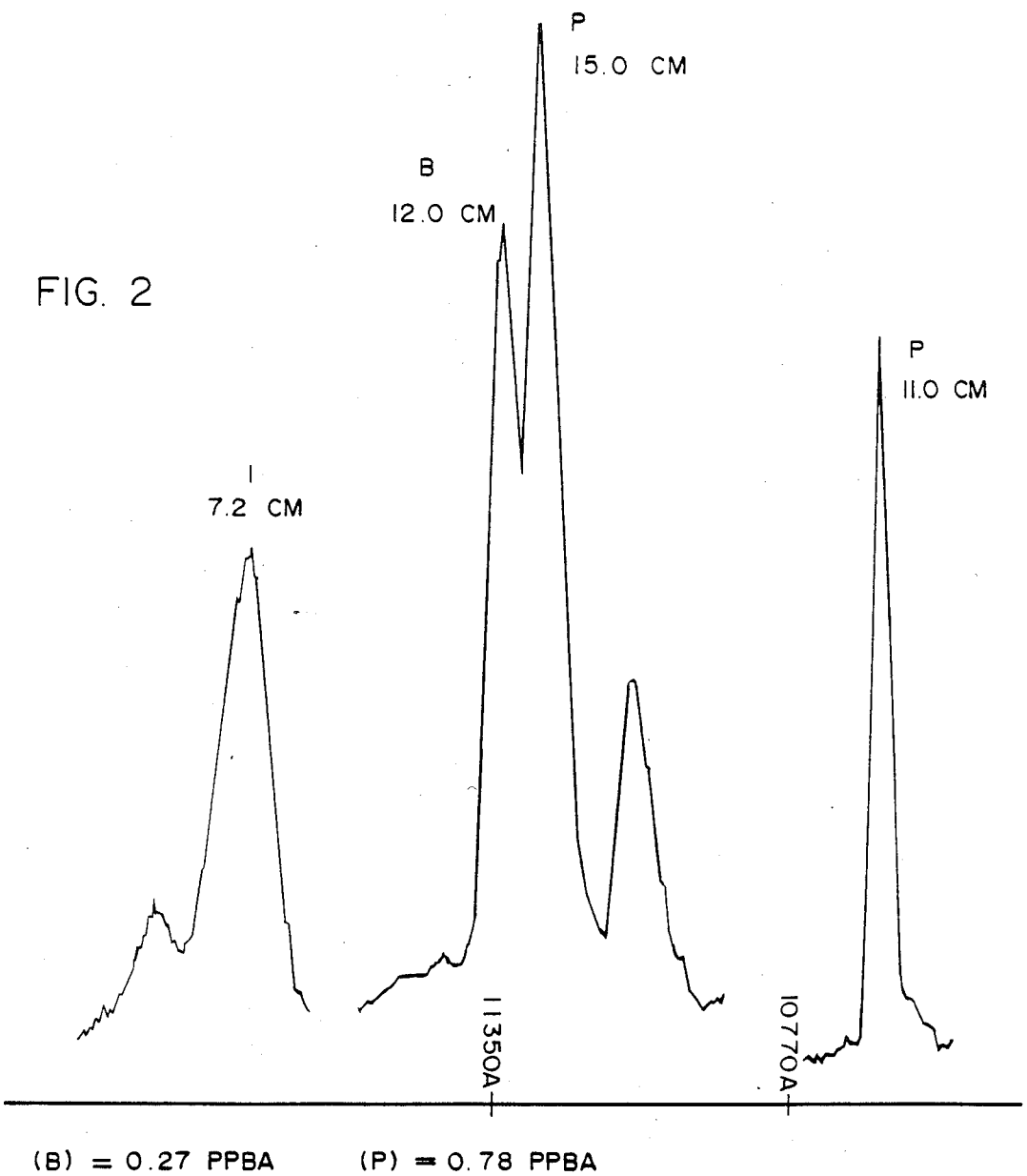

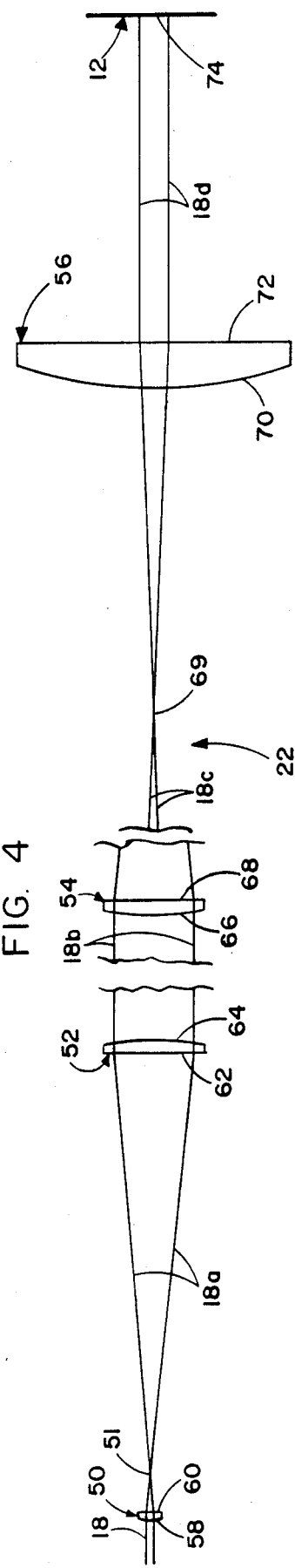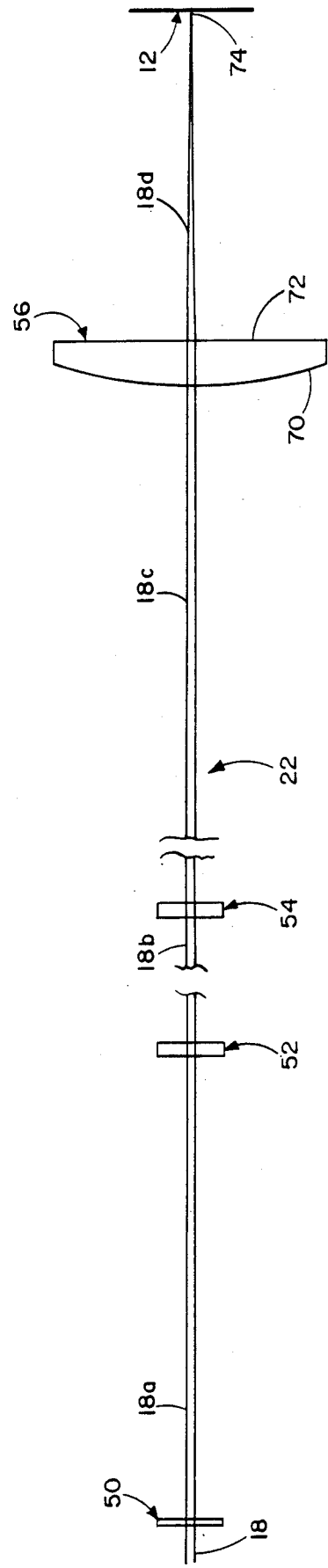
FIG. 4
FIG. 5

APPARATUS AND METHOD FOR PHOTOLUMINESCENT ANALYSIS

BACKGROUND OF THE INVENTION

This invention relates to the field of photoluminescent (PL) analysis, in which a light source is used to excite a sample, and the photons emitted by the sample are passed through a monochromator to a detector which provides a measurement of intensity.

The present invention is particularly valuable as a means of determining impurity concentrations in single crystal silicon (Si), but it also has other potential uses, such as dopant measurement in gallium arsenide. Generally, the impurities would be those unintentionally incorporated; but in some cases intentionally doped impurities would be measured. Such impurity determinations are a very important means of determining the characteristics of electronic devices in integrated circuit chips.

The use of PL analysis for this purpose is discussed in an article by Tajima in Applied Physics Letters (American Institute of Physics), Volume 32, No. 11, June 1, 1978 (Page 719), and in an article by Tajima and Nomura in Japanese Journal of Applied Physics, Volume 20, No. 10, October, 1981, (Page L-697). As pointed out in these articles, the PL technique "can be successfully applied to the characterization of silicon crystals as a powerful means for analysis of shallow impurities. The PL method makes it possible to detect non-destructively a small amount of impurities in a small region of a specimen". The cited articles point out that the concentration of an impurity is proportional to the ratio of the intensities of the impurity and intrinsic signals.

The use of PL analysis of silicon chips was discussed by L. W. Shive, of the Monsanto Company, in October 1981, at a meeting of ASTM F1.06, The Electrical and Optical Measurements Committee. It was point out that, in his experiments, PL analysis was "designed to analyze single crystalline silicon only"; and that the method "assays silicon for Group II B and V B impurities, that is boron, phosphorus, arsenic, aluminum, and antimony". As summarized by Shive, PL analysis basically involves three steps: (1) "low temperature photoexcitation of the silicon sample", (2) "light emission from the sample—luminescence", and (3) "detection of the emitted light. The luminescence is a result of carrier recombination which takes place within the silicon sample".

In discussing the apparatus used for experimental purposes, Shive stated: "A laser is used to photoexcite the sample—which is immersed in liquid helium. The light emitted by the sample is resolved by a monochromator, detected by a photomultiplier tube, amplified, and recorded. The sample luminesces continuously and a spectrum of intensities as a function of wavelength is recorded."

The very promising concepts discussed above are subject to the problem of getting as much light as possible from the sample through the monochromator and onto the photomultiplier tube. To do this, one must collect as much of the light being emitted by the sample as possible, and fill the monochromator's entrance aperture and acceptance cone with this light. The problem at first seems straight forward. One collects the light from the sample with a colliminating lens of low f number, then focuses the light onto the monochromator's entrance slit with a lens which matches the monochromator's acceptance f number. Since monochromators typically have f numbers between f/3 and f/5, the focusing lens can be a single element. With this pair of lenses, the solid angle requirements are met.

In the PL analysis systems heretofore used, only about 2% of the available sample-emitted light collected by the adjacent lens passes the entrance slit in the monochromator. The round spot illuminated by the laser (source of incident light at the sample), when transferred to the monochromator entrance slit, is still round. The slit, however, is long and narrow, e.g., approximately 0.012 mm×6 mm, causing a severe mismatch. Attempts to distort the spot image, to make it better match the slit, run afoul of the solid angle consideration which dictated the initial pair of lenses. Essentially, anything gained by changing the spot shape is lost by angular mismatch. One possible solution of the problem is the use of fiber optic image transformers. However, their low packing density (30%) and high cost make them unattractive.

SUMMARY OF THE INVENTION

The present invention provides, essentially, at least a five-to-one improvement in the percentage of sample-emitted, lens-collected light which passes the monochromator slit. In other words, from the 2% figure cited above, this invention has succeeded in raising to at least 10% the portion of such light which passes through the monochromator slit. (The invention is also applicable to other types of grating spectrometers.)

This significant result is accomplished by incorporating, between the energy supplying radiation source (generally a laser) and the sample which is photoexcited by the laser beam, an optical combination which shapes the laser excitation beam in such a way that, at the point where that beam is incident on the sample, the shape of the beam essentially matches, or is similar to, the shape of the monochromator slit. The beam shape may either be proportional, or substantially identical, to the shape of the slit.

The light emitted by the sample is preferably collected by a low f number lens located close to the sample, and then focused on the slit by a focusing lens which matches the monochromator's acceptance f number.

An advantageous feature of the optical system disclosed in this application is the dual use of the lens which is closest to the sample as a shaping collimating lens in directing the laser excitation light to the sample, and as a collecting/collimating lens in collecting the widely dispersed light emitted by the sample. This is accomplished by a "spherical" lens, or its equivalent, i.e., a lens which can be schematically represented as having a flat surface facing toward the sample, and a convex, spherically-shaped surface facing away from the sample. This lens constitutes, therefore, both an element in the pre-sample optical system and an element in the post-sample optical system. As a practical lens at the sample, a lens system is preferably used which has a plurality of lens elements designed to provide aberration-free optical performance.

Another advantage of the present PL system is the location of the Dewar aperture, through which excitation light enters, and sample-emitted light exits, at the bottom of the Dewar. This feature contributes greatly to the lens-to-sample closeness which is needed for optimum performance.

BRIEF DESCRIPTION OF DRAWINGS

FIGS. 1a, 1b and 1c illustrate the basic concepts involved in the utilization of intense light as the means for causing the emission of luminescent photons by a cooled semiconductor sample which contains dopants whose concentration is to be measured;

FIG. 2 shows an example spectrum derived by photoluminescence (PL) from a single crystalline silicon sample doped with both boron and phosphorus;

FIG. 3 shows schematically a PL system incorporating the present invention;

FIGS. 4 and 5 show a more detailed schematic of the "pre-sample" optical system, i.e., that part of the optical system in FIG. 3 which delivers illumination from a laser source of excitation light to the surface of the sample, FIG. 4 being a side view and FIG. 5 a top view of the same laser-to-sample lens system;

DETAILED DESCRIPTION OF A PREFERRED EMBODIMENT

Figure 6A:
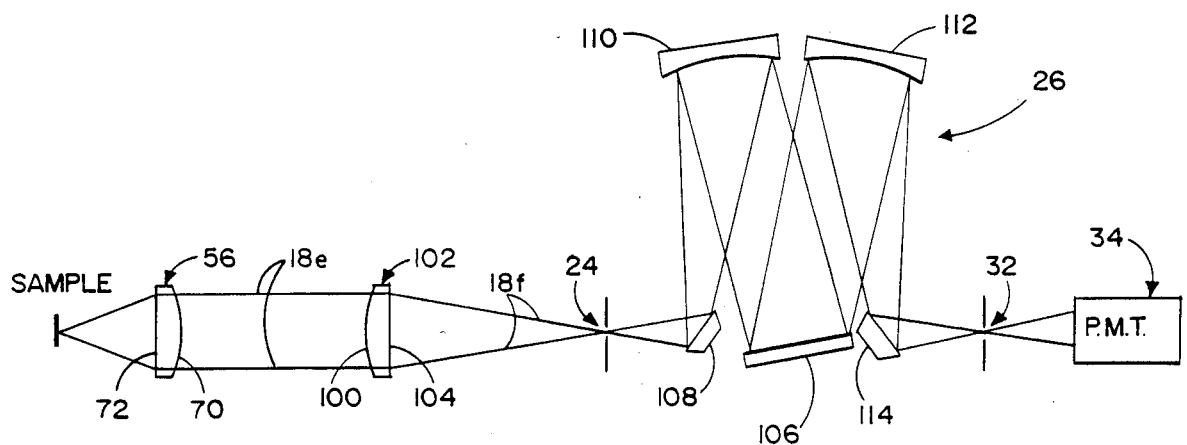
FIG. 6a shows a more detailed schematic of the "post-sample" optical system, i.e., the sample-to-detector part of the optical system included in the FIG. 3 PL system.

FIG. 1 is intended only to illustrate the theoretical basis of the PL system for measuring dopants in semiconductor materials. PL spectroscopy offers a method for measuring the group V donors phosphorus, arsenic, and antimony; and the group III acceptors boron and aluminum. The underlying physical process can be explained with the help of FIGS. 1a–1c. Since the impurities of interest all have low ionization potentials (approximately 1/10 eV), they are all fully ionized at room temperature. This is depicted in FIG. 1a. Cooling the sample to 4.5° K. results in the situation of FIG. 1b, which shows the net dopants neutralized. At this temperature, illuminating the sample with intense visible light will cause the situation shown in FIG. 1c. The visible light generates a high concentration of hole-electron pairs, which neutralizes the remaining impurities. FIG. 1c also shows some of the recombination processes which give rise to the luminescent photons. It is these photons which are used to measure the dopant concentration. Following the Tajima articles identified above, the dopant concentration can be given as a function of the ratio of the intensities of the dopant and intrinsic lines. Using the ratio of intensities makes the method immune to changes in sample preparation.

FIG. 2, which is taken from the material of Shive identified above, is the spectrum of a silicon sample doped with both boron and phosphorus. The line marked "I" is an intrinsic line, whereas "B" indicates boron and "P" phosphorus. In this spectrum, the concentration of boron is equal to 0.27 PPBA and the concentration of phosphorus is equal to 0.78 PPBA. The numbers next to each peak represent its measured height.

FIG. 3 shows the general layout of the PL system. A sample 12 is located in a Dewar flask 14, which may be maintained at the desired cryogenic temperature (e.g. 4.5° K.) by means of liquid helium. The excitation light may be provided by a laser 16, emitting a beam 18 which passes through a chopper 20, and is then shaped and impinged on the sample 12 by a pre-sample optical system indicated generally at 22, the details of which will be explained below.

The relatively dispersed PL light emitted by the sample 12 is collected and then focused at the entrance slit 24 of a monochromator 26 by a post-sample optical system indicated generally at 28, the details of which will be explained below.

A stepper motor 30 is provided to drive the grating of the monochromator, and the exit slit 32 of the latter directs the diffracted light to a photomultiplier tube 34. Detector tube 34 converts any light passed by the monochromator 26 into an electrical signal, which may be input to a preamplifier 36, which in turn sends the amplified signal to a synchronous demodulator 38. The output of demodulator 38 is input to a switched integrator 40 for minimum noise bandwidth. The output of integrator 40 is digitized by an analog-to-digital converter 42, and buffered onto a bus 44.

The control function is provided by a computer 46, which has control of the stepper motor 30, the integrator 40, and the A/D converter 42. Since the computer has access to all functions, the system has maximum flexibility because it is fully under software control.

As stated in discussing the background of this invention, prior systems of this type have only captured about 2% of the available sample-emitted light collected by the adjacent lens. This invention provides a very significant increase in the light available at the detector, primarily by means of the pre-sample optical system 22. This improved throughput, which has increased the 2% figure to at least 10%, can be used either to increase the operating speed, or to improve the accuracy of the analysis. Generally, speed increase will be emphasized.

FIGS. 4 and 5 show schematically the details of the pre-sample optical system, FIG. 4 being a side view, and FIG. 5 a top view. The concentrated beam 18 of excitation light emitted by the laser is reshaped by a plurality of lenses, which have the effect of spreading the beam 18 in one dimension, while shrinking it in the other dimension, until it eventually forms a narrow line matching the dimensions of the monochromator entrance slit 24, e.g., approximately 0.012 mm wide by 6 mm long. If desired, the design can be arranged to provide a shape at the sample 12 proportional to that of slit 24, rather than an identical shape. Furthermore, a pre-sample optical system 22 which causes the shape of the excitation light at the sample to tend to conform to the shape of the slit can significantly improve performance of the PL system, even though total conformity is not obtained.

Theoretically, the pre-sample optical system could be provided by only two lens elements, the first a cylindrical lens to "fan out" the laser beam 18, and the second a spherical lens to collimate the beam in its larger dimension and narrow it in its smaller dimension, thereby approximating the extreme ratio of the slit dimensions.

However, for a variety of design considerations (including the need to change beam direction to obtain compactness of the system), in a prototype system the pre-sample optical system comprises three "cylindrical" lenses 50, 52, and 54 and a "spherical" lens 56. The first lens 50 reached by the beam 18 has a cylindrically-shaped side 58 facing the laser beam and a flat side 60 facing toward the much larger second lens 52, which has its flat side 62 facing lens 50. The relatively small lens 50 directs a beam 18a toward the larger lens 52, which beam focuses at 51 and then fans out in one dimension only (the vertical dimension in FIG. 4). The cylindrically-shaped side 64 of lens 52 directs toward the facing cylindrically-shaped side 66 of lens 54 a wide flat beam 18b, which is seen as essentially a planar rectangle in FIGS. 4 and 5. From the flat side 68 of lens 54 the excitation beam 18c focuses at 69 and fans out to impinge on the spherical surface 70 of lens 56. The location of focal point 69 is dictated in part by the need (which will be explained in detail below) to have the beam pass through a small central hole in a reflecting mirror that is part of the post-sample optical system.

The spherical lens 56, which should be located as close as possible to the sample 12, has the dual effect on entering beam 18c collimating it in one dimension and shaping it in the other. The collimating effect is shown in FIG. 4, and the shaping effect in FIG. 5. Thus, the excitation beam 18d, which exits from the flat side 72 of lens 56, and impinges on the surface of sample 12 at 74, will have at 74 the desired shape designed to equal, or be proportional to the shape of the slit 24. The pre-sample optical system just described reshapes the laser beam, but the area of the beam at the sample remains substantially the same as its initial area, so that the energy density is essentially unchanged.

The light emitted by the sample, in accordance with the PL process discussed above, will be widely dispersed. By using lens 56 as the first lens in the post-sample optical system, and by designing it and locating it so as to collect as much as possible of the sample-emitted light, the efficiency on the PL system is greatly enhanced. The results of experimentation have demonstrated that it is difficult, if not impossible, to obtain a single-element lens 56 which is sufficiently aberration-free to provide the desired optical efficiency. Consequently, a multiple-element lens system is actually used as the lens 56. This lens, therefore, preferably should be a commercially available camera lens having a 50 mm focal length, an f number in the range of f/1.2 to f/1.5, and a resolution of at least 250–300 line pairs per millimeter. The word "lens", as used in the optical art, and as used in this application, covers either a single-element or a multiple-element lens arrangement which is designed and supplied as a unit, and is so constructed as to have the desired optical characteristics.

Figure 7:
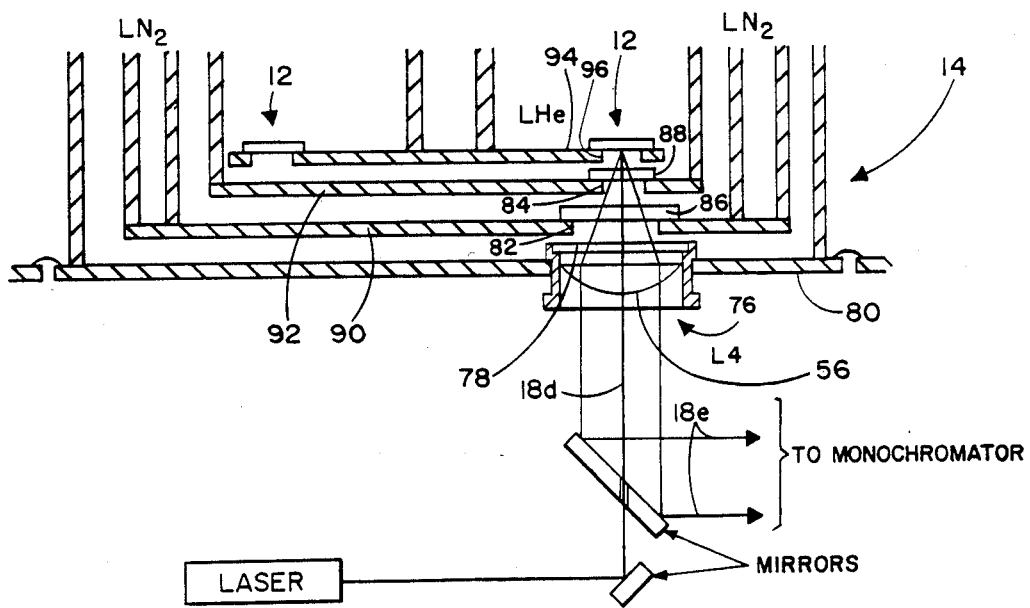
FIG. 7 shows an example of a Dewar configuration containing the cooled sample, and its adjacent optics.

Limitations are created on the amount of available sample emitted light by the necessity of locating the sample 12 in a Dewar flask. However, the efficiency and convenience of the Dewar arrangement are maximized by locating the Dewar above the optical system, and locating the light aperture in the bottom of the Dewar, a feature which both simplifies the design of the Dewar structure and enhances the collection of the sample-emitted light. The Dewar light aperture, and the location of the sample in the Dewar, are shown in FIG. 7 which is a sectional view in a vertical plane.

Both the pre-sample optical system 22 and the post-sample optical system 28 (FIG. 3) are preferably supported on a horizontal platform. The Dewar 14, which is a cylindrical vessel, is preferably located directly above lens 56, and beam 18d from lens 56 is directed upwardly. As shown in FIG. 7, the lens 56 is preferably mounted as a recessed inset in the bottom plate of the Dewar. The beam 18d enters the Dewar through an aperture 76 covered by a window 78 supported on the bottom plate 80 of the Dewar. A plurality of decreasing diameter apertures 82 and 84, covered respectively by windows 86 and 88, are provided in successive Dewar plates 90 and 92. The sample 12 is supported on the innermost horizontal Dewar plate 94, which has an aperture 96. Another sample 12 is shown near the left edge of plate 94, the Dewar preferably being designed to hold a substantial number of samples, e.g., 20, all carried by a holder which is rotated to bring successive samples into the measurement position. As can be seen, the samples always remain normal to the optical axis; and therefore, the holder does not require precise rotation.

FIG. 6a shows schematically the post-sample optical system. As previously stated, the system is designed to maximize the extent to which the widely dispersed photons emitted by the sample 12 are collected by the same lens 56 which focuses the excitation light from laser 16 on the sample. Since the photons emitted by the sample are widely scattered, the collecting, or condensing lens 56 should have a large diameter and be as close as possible to the sample 12. And, as previously stated, the fact that a "downward looking" Dewar 14 is used, permits the lens 56 and sample 12 to be much closer than would be possible with a different Dewar arrangement. Since lens 56 is a large diameter lens located close to the sample, it must, as previously stated, have a low f number.

Figure 6B:
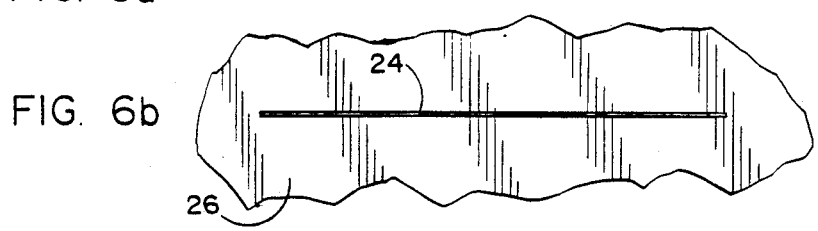
FIG. 6b is an enlarged view illustrating the fact that the monochromator slit in FIG. 6a has an extremely high length-to-height ratio.

As seen in FIG. 6a, the sample-emitted light collected by the flat side 72 of lens 56 forms a collimated beam 18e between the spherical face 70 of lens 56 and the spherical face 100 of another spherical lens 102, which is located nearest to the monochromator slit 24. The beam 18f which emanates from the flat side 104 of spherical lens 102 focuses at the monochromator slit 24 an image having the same general shape as the slit, thereby providing the maximum available energy at the slit, which constitutes the limiting factor in the amount of energy throughput available to the detector 34. FIG. 6b is an enlarged view looking at the wall in which slit 24 is formed, emphasizing its very large length-to-height ratio.

In order not to waste any of the available slit aperture acceptance angle, it is considered desirable to slightly "overfill" the slit by having lens 102 re-image the sample onto the entrance slit 24 at f/3, whereas the acceptance angle of the selected monochromator 26 is f/4.2. The monochromator 26 comprises a grating 106, which is moved by stepper motor 30 (FIG. 3), and a plurality of fixed reflectors 108, 110, 112 and 114.

Figure 8:
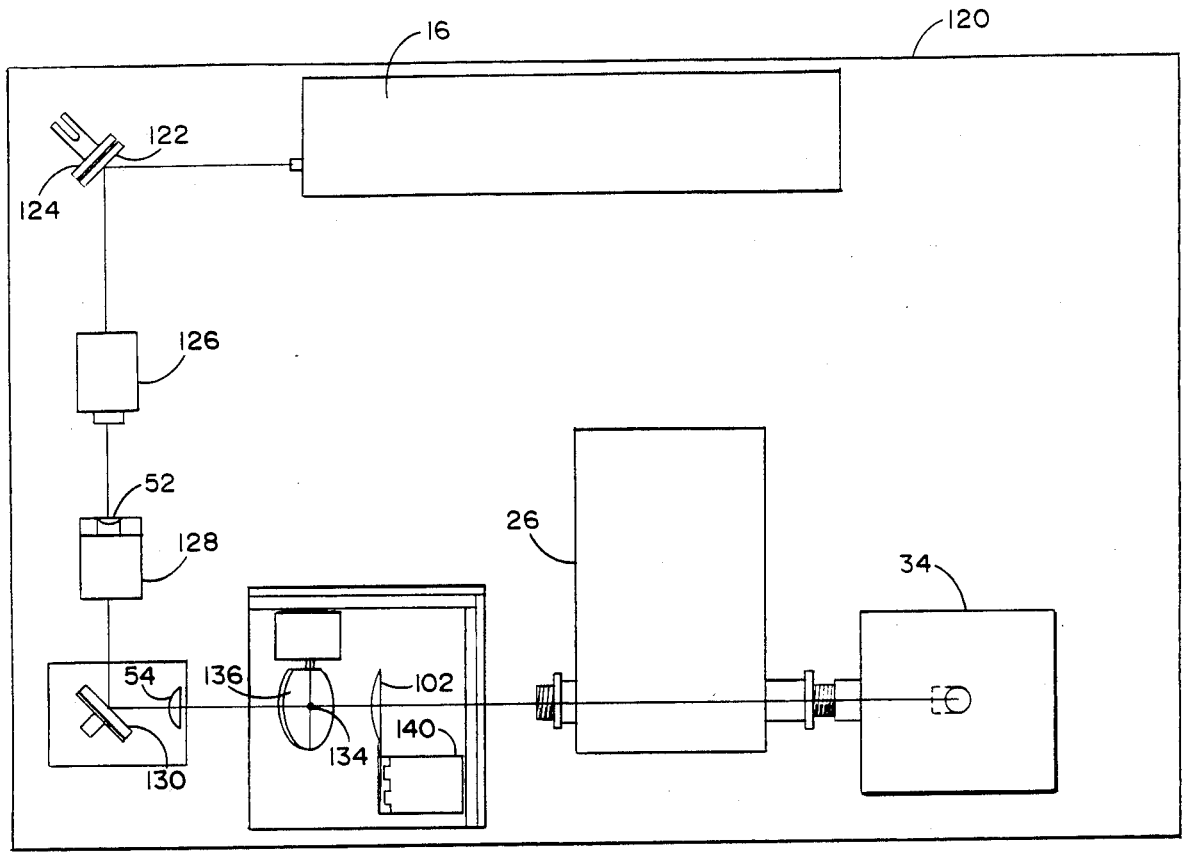
FIG. 8 is a plan view showing a physical embodiment of the PL system described in this application; and, FIG. 9 is an elevation view showing the system of FIG. 8 from one side.
Figure 9:
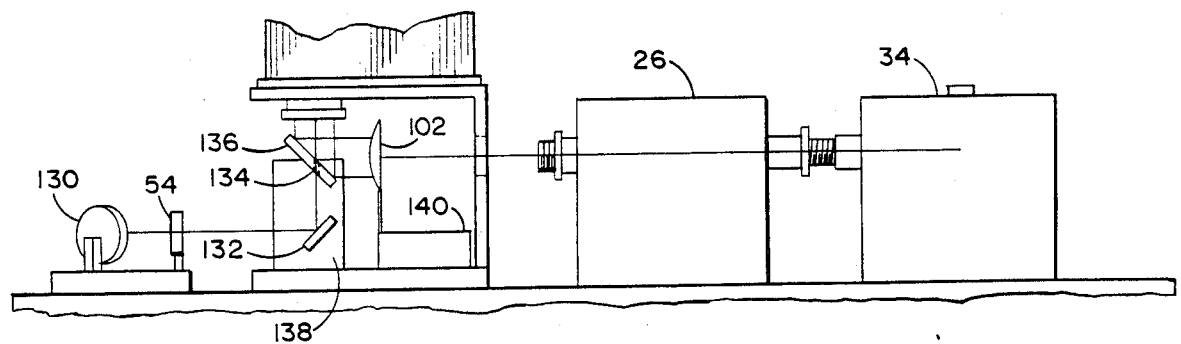

As will be apparent from the description of FIGS. 8 and 9, the actual optical system of the prototype requires several additional optical elements and features for design compactness and convenience. But, the essential features have been included in the foregoing description.

The system as a whole includes components whose characteristics may be varied to suit particular requirements, but a preferred combination appears to have the following features. The monochromator may be an ISA model HR-320, having f/4.2 optics. This unit is compact and has a high throughput. The grating preferably has a blaze angle set for a 1 micron wavelength. The monochromator selection is determined by the resolution needed as a system parameter. Since no two spectral features are closer together than 1.5 Å°, the monochromator needs to have the highest throughput which can resolve 1 Å°. This dictates an instrument in the ½ meter focal length class. Because the interesting spectral features for Si are all between 1.070 and 1.14 microns wavelength, an S1 photomultiplier is preferred as the detector 34. In the prototype, the tube used is an $LN_2$-cooled E.M.I. S1 end-looker, cooled to $-100°$ C. by locating it in a suitable Dewar.

The laser generator 16 preferably is a medium power argon ion laser, such as Lexel 0.5 watt model 85. It requires only single phase 208 V ac power, puts out the required 200 mw at 0.51 micron, and is compact and reliable. The windows 78, 86 and 88 of Dewar 14 preferably are clear fused quartz, anti-reflection coated for 1.0 micron wavelength. The middle window 86 intercepts the 300° K. radiation from the outer window 78. Since it re-radiates at 77° K., the inner window 88 sees only a small fraction of the thermal radiation it would otherwise receive. In other words, the holding time of the liquid helium is effectively doubled by inclusion of the middle window 86. In the post-sample optical system, the lenses 56 and 102 should be anti-reflection coated for a wavelength of 1.0 micron. In the pre-sample optical system, the lenses 50, 52 and 54 should be anti-reflection coated for a wavelength of 0.5 micron.

FIGS. 8 and 9 show the general structure of the prototype system. In the plan view (FIG. 8), the laser generator 16 is shown at the top of the figure, mounted on a platform 120, such as an NRC table. The laser radiation is reflected by a flat mirror 122, set at a 45° angle, and carried by a mirror mount 124 which permits initial position adjustment by tilting on two axes (vertical and horizontal). The mirror mount 124, and all the other optical element carriers may be supported by suitable brackets secured to table 120. A holder 126 may carry both the chopper 20 and the first, very small cylindrical lens 50 (neither of which are seen in FIG. 8). Lens 50 should be so mounted as to have displacement (translation) adjustment in two axes. The next cylindrical lens 52, which is shown carried by a holder 128, requires only vertical displacement adjustment. The combination of lenses 50 and 52 functions as an "up-collimator", the lens size ratio being about 10 to 1. A second flat mirror 130, which may be identical in structure and adjustability to mirror 122, is set at a 45° angle to reflect radiation from lens 52 toward lens 54, the third cylindrical lens. This lens also requires initial position adjustability by displacement along a vertical line.

Since the Dewar is located above the optical system, radiation from lens 54 is deflected upwardly by a flat mirror 132 (see FIG. 9), which is set at an angle of 45° with respect to the vertical, thus changing the beam direction from horizontal to vertically upward. The vertical beam passes through an aperture 134 in another flat mirror 136, which is part of the post-sample optical system. The location of the aperture 134 with respect to the pre-sample optical system should be at the focal point 69 (see FIG. 4) between the cylindrical lens 54 and the spherical lens 56 which is mounted in the bottom of Dewar 14. The mirror reflector 132 should have two-axis tilt adjustability. Lens 56 which, as previously stated, is preferably a high quality camera lens containing multiple lens elements, requires only focus adjustment.

The mirror 136, which receives post-sample light emissions from lens 56, may be mounted on the same supporting member 138 as mirror 132, but it requires a separate adjustable mount having two-axis tilt adjustability. The post-sample radiation is reflected by mirror 136, which is set at an angle of 45° to the vertical, thereby changing the beam direction from vertically downward to horizontal. This horizontal beam passes through the final focusing spherical lens 102, which may actually be a single element plano-convex lens, and which should be so mounted as to have translation adjustability along three axes. This adjustability may be obtained conveniently by using three translation stages mounted on a single supporting member 140.

Radiation from spherical lens 102 is focused on the slit 24 of monochromator 26. And, for the reasons explained above, such radiation has been shaped to be similar to the shape of the slit, thereby substantially increasing the radiation throughput which enters the monochromator and reaches the photo-detector 34.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. In a system for determining the intensity of photoluminescence emitted at the surface of a sample, such system having in its input portion a laser radiation source which provides a highly concentrated, essentially circular beam of radiation for sample-excitation purposes, and having in its output portion a photodetector and a grating spectrometer which receives sample-emitted radiation at its entrance slit and sends radiation through its exit aperture to the photodetector; an optical apparatus, operative between the source of excitation radiation and the grating spectrometer, comprising:

pre-sample optical means for reshaping the laser beam radiation in such a way that it has cross-sectional dimensions proportionally similar to those of the grating spectrometer slit at the location of excitation contact of the laser beam with the sample, the pre-sample optical means including (a) a first optical element which widens the laser beam in one dimension, and (b) a second optical element which receives the laser beam from the first optical element and narrows the beam in the other dimension; and post-sample means for collecting the radiation emitted by the sample as a result of such excitation and focusing such collected radiation in such a way that its cross-sectional dimensions at the grating spectrometer entrance slit are similar to those of the slit, the post-sample optical means including (a) a first optical element which collects the relatively dispersed radiation emitted by the sample, and (b) a second optical element which focuses the radiation collected by the first optical element on the grating spectrometer entrance slit;

a single dual-purpose lens constituting both the second optical element of the pre-sample optical means and the first optical element of the post-sample optical means.

2. The optical apparatus of claim 1 wherein the dual-purpose lens acts as a shaping and collimating lens in the pre-sample optical means, and as a collecting and collimating lens in the post-sample optical means.

3. The optical apparatus of claim 1 or claim 2 wherein the dual-purpose lens is the optical element closest to the sample, and has a flat surface facing toward the sample and a spherically-shaped surface facing away from the sample.

4. In a system for determining the intensity of photoluminescence emitted at the surface of a sample, such system having in its input portion a laser radiation source which provides a highly concentrated, essentially circular beam of radiation for sample-excitation purposes, and having in its output portion a photodetector and a grating spectrometer which receives sample-emitted radiation at its entrance slit and sends radiation through its exit aperture to the photodetector; a method of enhancing radiation throughput to the photodetector comprising the steps of:

reshaping the laser beam in such a way that it has cross-sectional dimensions proportionally similar to those of the grating spectrometer slit, by first widening the laser beam in its one cross-sectional dimension and thereafter narrowing the laser beam in its other cross-sectional dimension;

causing the reshaped laser excitation beam to impinge on the surface of the sample;

collecting the radiation emitted by the sample as a result of the excitation effect of such refocused laser beam; and focusing such collected radiation in such a way that its cross-sectional dimensions at the grating spectrometer entrance slit are similar to those of the slit;

a single dual-purpose lens being used to accomplish both the final shaping of the pre-sample laser radiation beam which impinges on the sample, and the collecting of the sample-emitted radiation.

* * * * *